United States Patent
Yamaguchi et al.

[11] Patent Number: 5,570,409
[45] Date of Patent: Oct. 29, 1996

[54] APPARATUS FOR X-RAY FLUOROSCOPY AND FLUOROGRAPHY

[75] Inventors: Shojiro Yamaguchi; Hajime Takemoto, both of Kyoto, Japan

[73] Assignee: Shimadzu Corporation, Japan

[21] Appl. No.: 524,247

[22] Filed: Sep. 6, 1995

[30] Foreign Application Priority Data

Oct. 31, 1994 [JP] Japan .................................. 6-292131

[51] Int. Cl.$^6$ ...................................................... H05G 1/02
[52] U.S. Cl. .......................................... 378/196; 378/209
[58] Field of Search ...................................... 378/195, 196, 378/209, 19, 68, 177

[56] References Cited

U.S. PATENT DOCUMENTS

| | | | |
|---|---|---|---|
| 3,096,976 | 7/1963 | Kierner et al. | 378/209 X |
| 3,441,266 | 4/1969 | Rossi | 378/209 X |
| 3,778,049 | 12/1973 | Viamonte, Jr. | 378/209 X |
| 3,831,032 | 8/1974 | Putod | 378/195 |
| 4,731,889 | 3/1988 | Ishikawa | 378/209 X |
| 4,908,844 | 3/1990 | Hasegawa | 378/209 X |
| 5,014,292 | 5/1991 | Siczek et al. | 378/209 X |
| 5,412,823 | 5/1995 | Sitta | 378/209 X |

*Primary Examiner*—David P. Porta
*Attorney, Agent, or Firm*—Majestic, Parsons, Siebert & Hsue

[57] ABSTRACT

An apparatus for X-ray fluoroscopy and fluorography includes not only a supporting column for supporting X-ray radiating and detecting devices opposite each other, a top board supporting member supporting a top board above the X-ray detecting device, and a base for supporting the top board supporting member which is movable vertically and rotatable around a horizontal axis, but also a rotary member which is disposed between the top board supporting member and the base and is rotatable around the horizontal axis, a device for rotationally driving the rotary member, guide rails extending vertically and attached to a side surface of the rotary member facing the base, a parallel-moving base attached to the top board supporting member and movable along the guide rails, and a parallel-moving device for moving the parallel-moving base vertically.

3 Claims, 4 Drawing Sheets

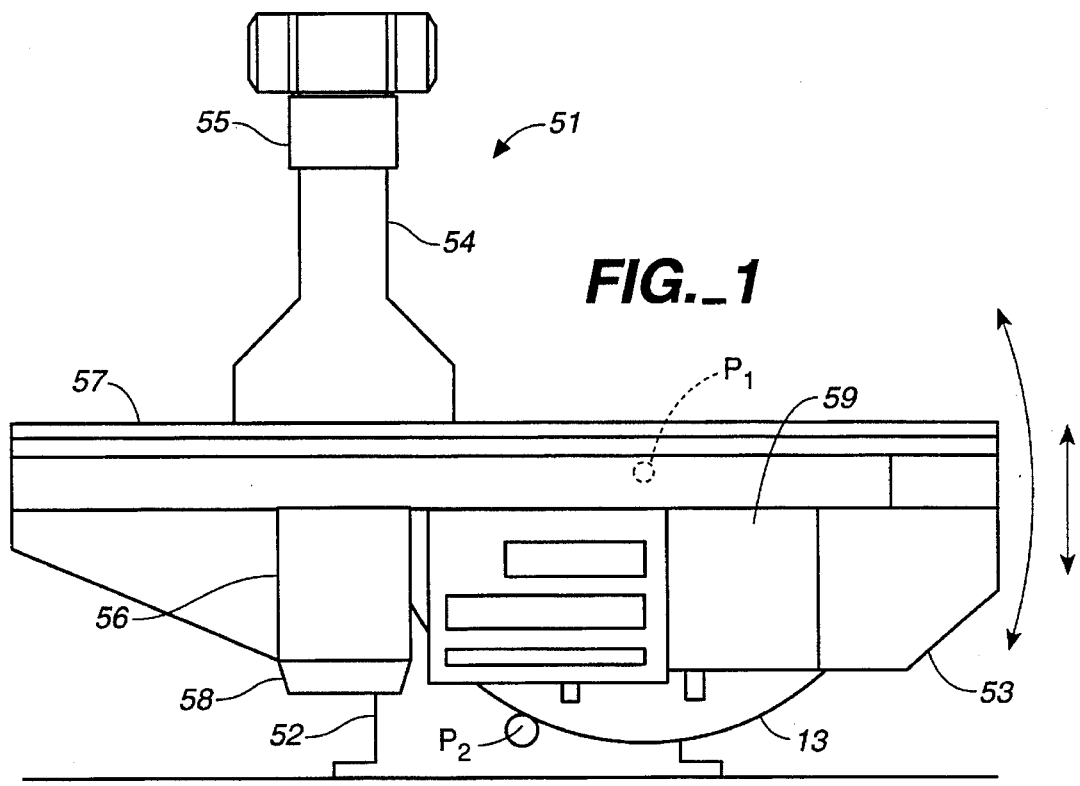
FIG._1
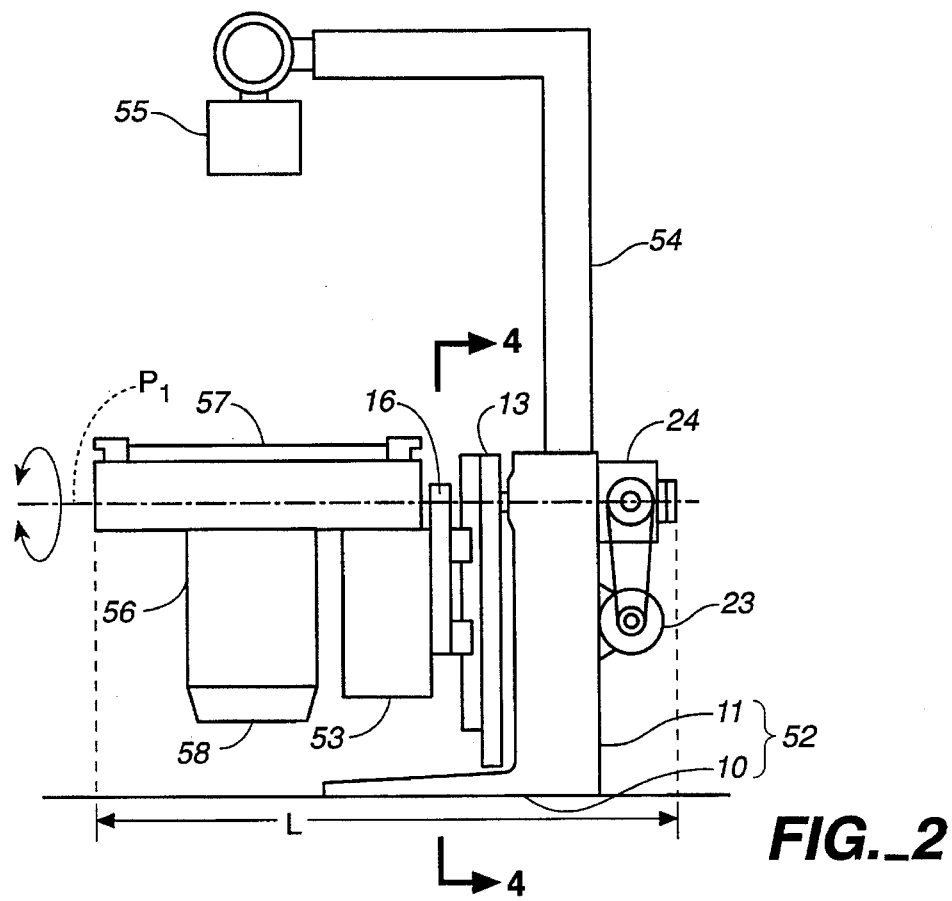
FIG._2

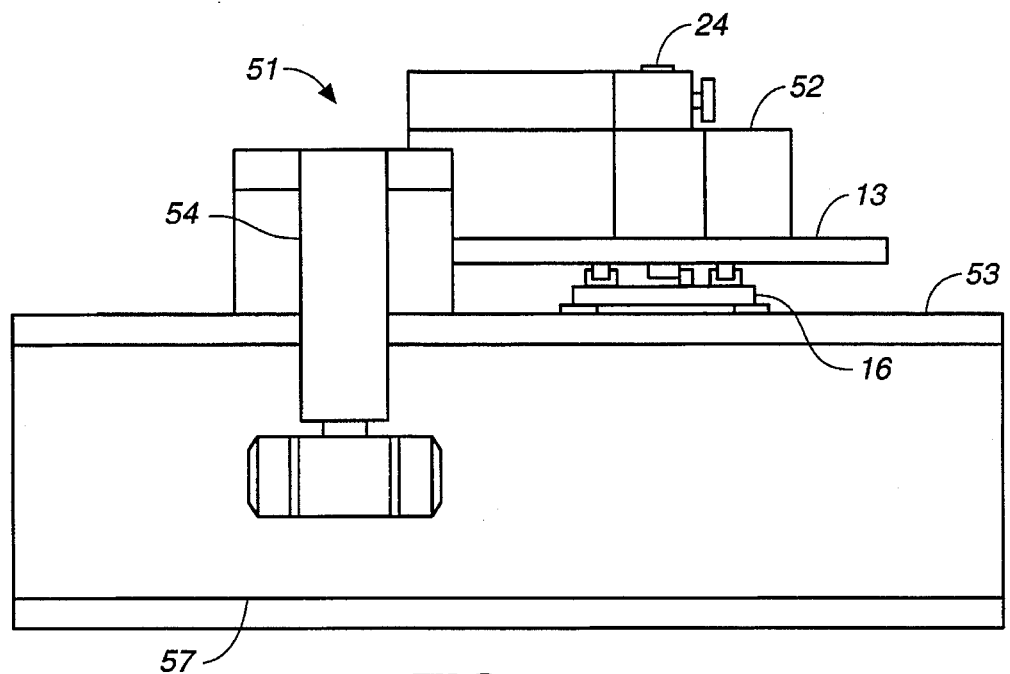
FIG._3
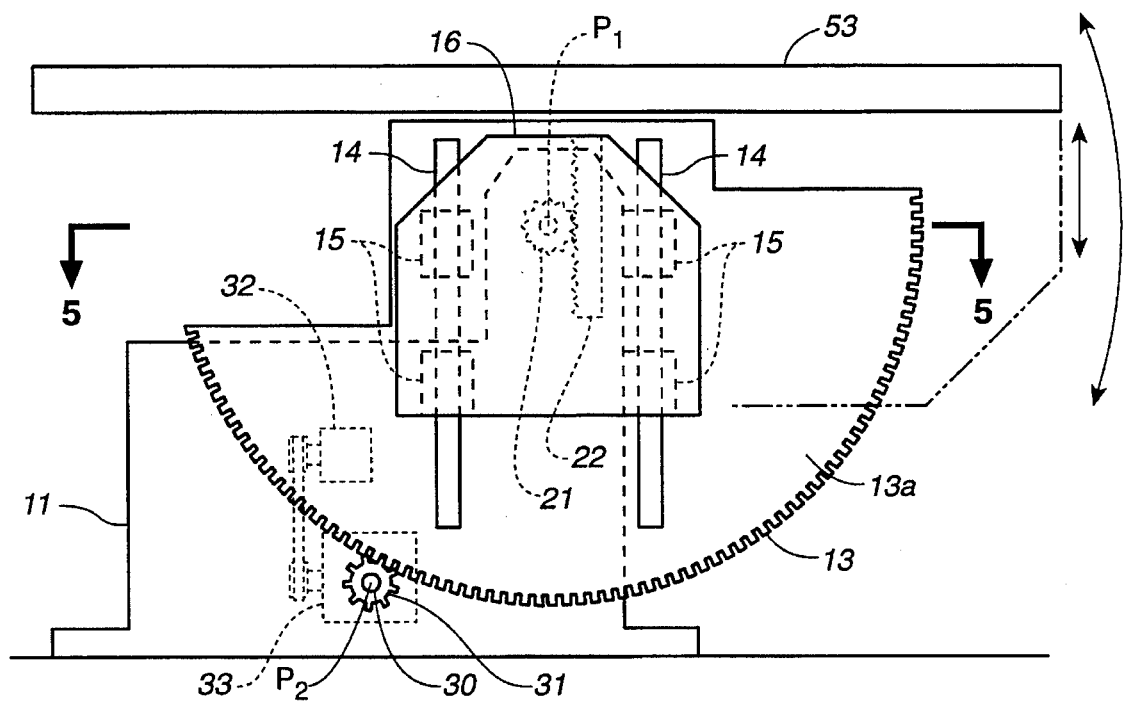
FIG._4

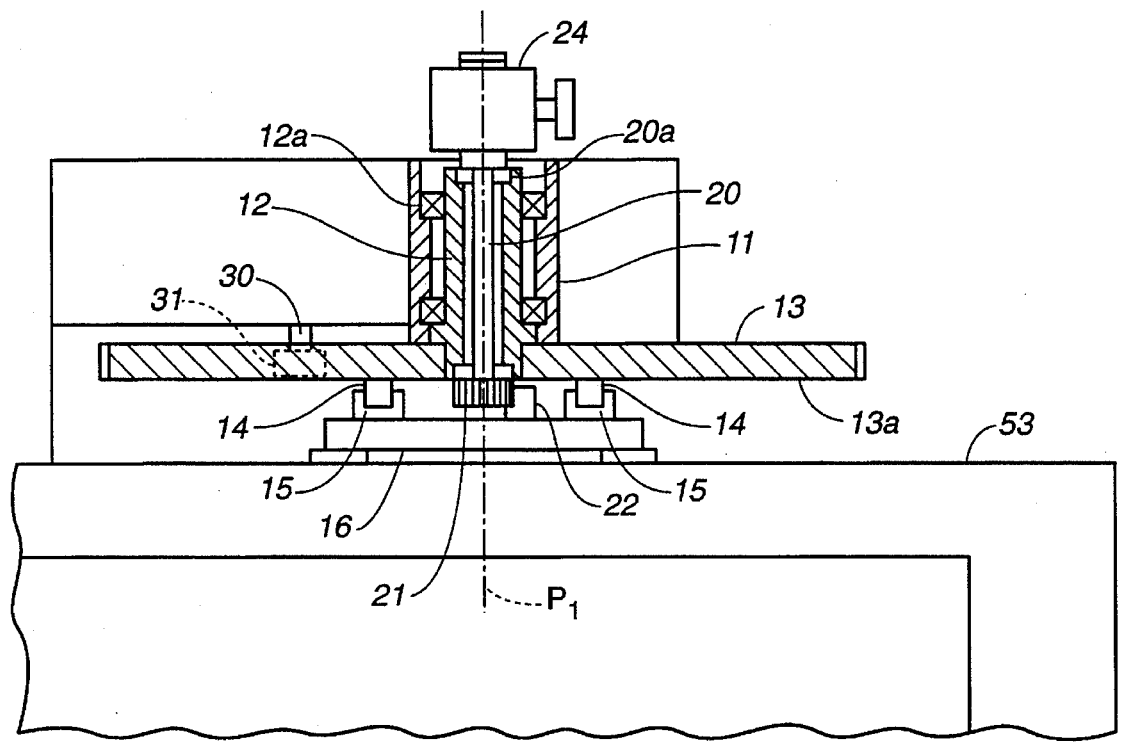
FIG._5
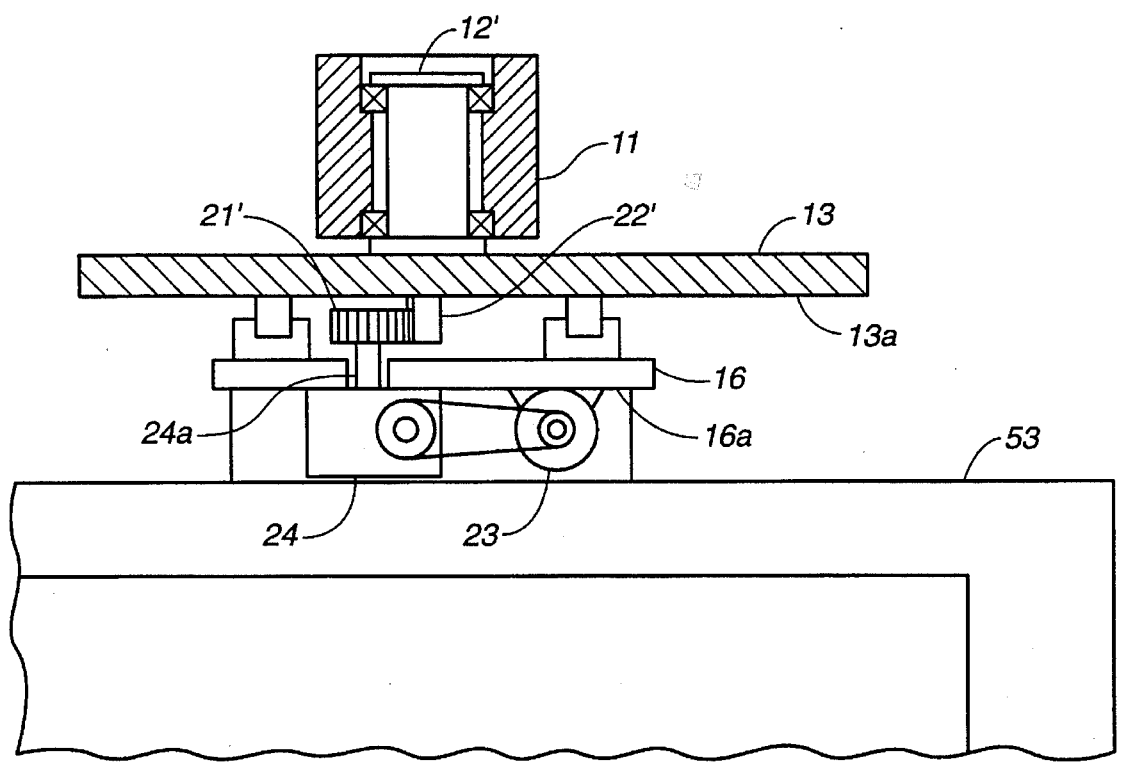
FIG._6

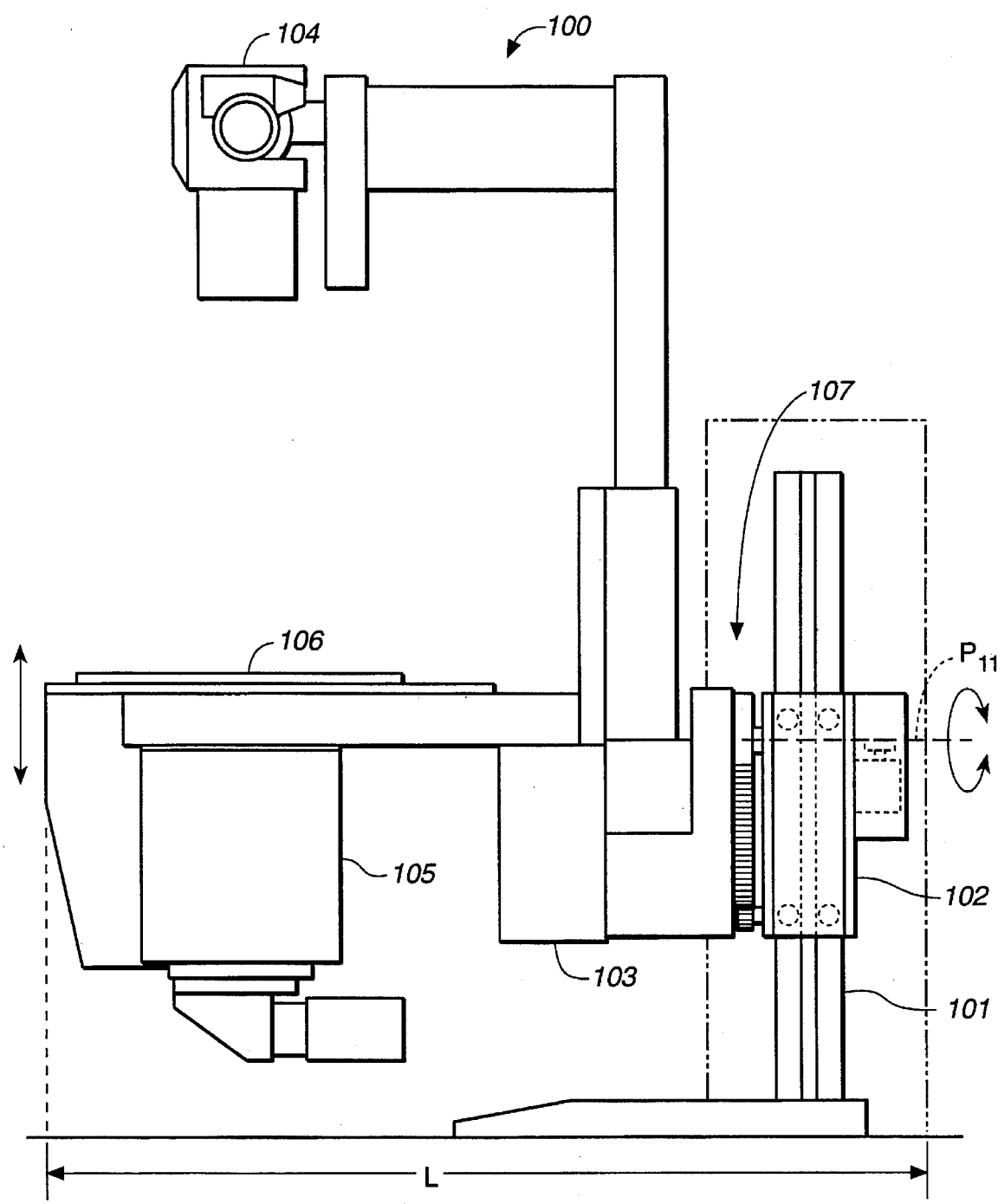
FIG._7
*(PRIOR ART)*

APPARATUS FOR X-RAY FLUOROSCOPY AND FLUOROGRAPHY

BACKGROUND OF THE INVENTION

This invention relates to an apparatus for X-ray fluoroscopy and fluorography comprising a main frame which is provided with X-ray radiating and detecting means and supported by a base so as to be movable vertically and rotatable around a horizontal axis, as well as a top board disposed between the X-ray radiating and detecting means.

Apparatus of this type, having an X-ray tube above the top board for placing the target subject thereon, have been disclosed, for example, in Japanese Patent Publication Tokkai 6-30920. FIG. 7 shows an apparatus 100 of this kind, having a base 101 set on a floor, a frame 102 which is vertically movable with respect to it, and a main body frame 103 which is supported by the movable frame 102 rotatably around an axis $P_{11}$. An X-ray radiating device 104 and an image intensifier 105 are attached to the main body frame 103 opposite to each other, and a top board 106 is attached to the main body frame 103 so as to be between the X-ray radiating device 104 and the image intensifier 105. When a target subject is to be placed on the top board 106, the main body frame 103, to which is attached the top board 106, is lowered such that the positioning of the target subject thereon can be effected easily.

A prior art apparatus thus structured is disadvantageous in that its front-to-back dimension L is large because both a rotary mechanism 107 for rotation around the axis of rotation $P_{11}$ and the vertically movable frame 102 are disposed next to each other at the back side of the apparatus (that is, the right-hand side in FIG. 7). This means that the apparatus as a whole cannot be made compact.

SUMMARY OF THE INVENTION

It is therefore an object of this invention to provide an apparatus for X-ray fluoroscopy and fluorography with a reduced front-to-back dimension such that the apparatus as a whole can be made compact.

An apparatus according to this invention, with which the above and other objects can be accomplished may be characterized as comprising not only a supporting column for supporting means for radiating and detecting X-rays opposite each other, a top board supporting means for supporting a top board above said means for detecting X-rays, and a base for supporting said top board supporting means in a vertically movable manner and rotatably around a horizontal axis, but also a rotary member which is disposed between said top board supporting means and said base and is rotatable around said horizontal axis, means for rotationally driving said rotary member, guide rails extending vertically and attached to a side surface of said rotary member on the side of said base, a parallel-moving base attached to said top board supporting means and movable along said guide rails, and parallel-moving means for causing said parallel-moving base to move vertically.

When a subject person for examination is set on the top board, the parallel-moving means is activated to lower the parallel-moving base along the guide rails and to thereby bring down the top board supporting means and the top board to a desired lower height. Thereafter, the parallel-moving base is raised along the guide rails to bring the top board supporting means and the top board to a desired height for examination. When the body orientation of the subject person is to be changed, the rotationally driving means is activated to rotate the rotary member around the horizontal axis of rotation such that the top board supporting means is rotated therearound together.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a front view of an apparatus for X-ray fluoroscopy and fluorography according to this invention;

FIG. 2 is a side view of the apparatus of FIG. 1;

FIG. 3 is a plan view of the apparatus of FIGS. 1 and 2;

FIG. 4 is a sectional horizontal view taken along line 4—4 of FIG. 2;

FIG. 5 is a sectional plan view taken along line 5—5 of FIG. 4;

FIG. 6 is a sectional plan view of a part of another apparatus for X-ray fluoroscopy and fluorography according to a different embodiment of this invention; and FIG. 7 is a side view of a prior art apparatus for X-ray fluoroscopy and fluorography.

DETAILED DESCRIPTION OF THE INVENTION

An example of apparatus for X-ray fluoroscopy and fluorography according to this invention, as shown at 51 in FIGS. 1–3, comprises a base 52, which is set on a floor, and a main body frame 53, which is supported by the base 52 and is both movable vertically and rotatable around a horizontal axis $P_1$. A supporting column 54, which is U-shaped when seen sideways as shown in FIG. 2, is attached to the main body frame 53, supporting opposite to each other an X-ray radiating device 55 (including an X-ray tube and an X-ray collimator) and an image intensifier 56 serving as an X-ray detecting means. A top board 57 is supported also on the main body frame 53, positioned between the X-ray radiating device 55 and the image intensifier 56. The top board 56 is adapted to be displaceable in its longitudinal direction such that a change in the body orientation and the positioning of the target subject can be effected easily in the case, for example, of an examination using an imaging agent.

The base 52 is composed of a fixed base part 10 adapted to be affixed to a floor and a cylindrical support column 11 standing on the fixed base part 10. As shown in FIG. 5, a hollow rotary shaft 12 is supported by a plurality of bearings 12a at an upper part of the support column 11 so as to be rotatable around the horizontal axis $P_1$. A fan-shaped rotary gear 13 is attached to one end of this hollow rotary shaft 12 so as to be in a motion-communicating relationship therewith and to rotate together therewith around the axis $P_1$. A pair of guide rails 14 is attached to the side surface 13a of this gear 13 facing the main body frame 53 so as to be in the vertical direction when the gear 13 is horizontal, that is, when the top board 57 is horizontal, as shown in FIG. 1. These guide rails 14 are attached to the gear 13 so as to sandwich the axis of rotation $P_1$ therebetween and supports a parallel-moving base 16 by a plurality of guide members 15 such as linear bearings. The main body frame 53 is attached to this parallel-moving base 16 so as to be able to move vertically together therewith along the guide rails 14.

Inside the hollow rotary shaft 12 is a central rotary shaft 20 supported by a plurality of bearings 20a so as to be rotatable around the horizontal axis $P_1$. In other words, both the hollow rotary shaft 12 and the central rotary shaft 20 are rotatable independently of each other. A pinion 21 is attached to one end of this central rotary shaft 20 so as to rotate therewith, and a rack gear 22 engaging with this pinion 21 is attached to the parallel-moving base 16 along the pair of guide rails 14. The other end of the central rotary shaft 20 is connected together to a reciprocally operable electric motor 23 and a decelerator 24 such that the rotary motion of this motor 23 is communicated to the pinion 21 through the decelerator 24. As the pinion 21 is rotated, the rack gear 22 to which it is engaged causes the main body frame 53 to move vertically upward or downward along the support column 11 with the guide members 15 sliding against the guild rails 14.

As shown in FIG. 4, a rotary shaft 30 is supported by the support column 11 rotatably around another horizontal axis $P_2$ on the front side of the support column 11 near the floor. Another pinion 31, engaging with the rotary gear 13, is attached to one end of this rotary shaft 30. Another reciprocally operable electric motor 32 and another decelerator 33 for driving this pinion 31 are together connected to the other end of the rotary shaft 30 such that the rotary motion of the motor 32 is communicated to the pinion 31 through the decelerator 33. The rotary motion of the pinion 31 is communicated to the rotary gear 13, causing the main body frame 53 to be displaced around the horizontal axis P1 through the guide rails 14, the guide members 15 and the parallel-moving base 16.

As described above, the X-ray radiating device 55 and the image intensifier 56 are attached to the main body frame 53 through the supporting column 54. A television camera 58 for monitoring is disposed below the image intensifier 56, as shown in FIGS. 1 and 2. The image intensifier 56, the television camera 58 and the top board 57, which are supported by the main body frame 53, are thus all adapted to move vertically as well as around the axis of rotation $P_1$ unitarily with the main body frame 53 by the operation of the parallel-moving base 16 and the rotary gear 13. In FIG. 1, numeral 59 indicates a fast-operating camera device of the cassette-less type for recording X-ray images.

It is to be noted, with reference in particular to FIGS. 2 and 3, that the X-ray apparatus 51 according to this invention has a reduced front-to-back dimension L and can be made compact, as compared to the prior art apparatus shown in FIG. 7, because the vertical motion of the main body frame 53 is effected by means of the parallel-moving base 16 along the guide rails 14 attached to the rotary gear 13. Since the horizontal axis of rotation $P_1$ is placed away from the center of the top board 57 and closer to one of its edges from the side of the supporting column 54, as shown in FIG. 1, it is unnecessary to set the center of rotation of the top board 57 high and the base 52 can be made low. In other words, when the subject of examination is put in a standing position, the angle of rotation of the main body frame 3 (indicated as clockwise rotation in FIG. 1) is set large but, since the distance between the horizontal axis of rotation $P_1$ and the right-hand edge (with reference to FIG. 1) of the main body frame 53 is reduced according to this invention, the main body frame 53 is less likely to hit the floor, and hence the base 52 can be made lower. As for the rotation of the main body frame 53 in the reverse direction (indicated as counter-clockwise rotation in FIG. 1), the relatively longer distance between the horizontal axis of rotation $P_1$ and the left-hand edge (with reference to FIG. 1) of the main body frame 53 presents no significant disadvantage because the maximum angle of rotation set in this direction is small.

When a subject person for examination is set on the apparatus 51 thus structured, the top board 57 is oriented horizontally as shown in FIG. 1, and the motor 23 for parallel motion is activated to communicate its rotary motion through the decelerator 24 to the pinion 21 to rotate it in the clockwise direction with reference to FIG. 4. This rotary motion of the pinion 21 is communicated through the rack gear 22 to the parallel-moving base 16 such that the top board 57 is lowered to a desired height. After the subject person is placed on the top board 57, the motor 23 is rotated in the opposite direction to raise the top board 57 to a specified height.

When the subject person is to be set in a standing position, for example, for an examination using an image-forming agent, the motor 32 for rotary gear motion is activated. The rotary motion of this motor 32 is communicated through the decelerator 33 to the pinion 31, and the rotary gear 13 is rotated around the horizontal axis $P_1$, until the top board 57 is sloped by a desired angle.

Although the invention has been described above by way of only one example having a central rotary shaft 20 inside a hollow rotary shaft 12 to move the main body frame vertically upward and downward, this is not intended to limit the scope of this invention. FIG. 6 shows another embodiment of this invention characterized as having a motor 23 and a decelerator 24 for the parallel motion set on the front surface 16a of the parallel-moving base 16 and connecting a pinion 21' to the output shaft 24a of the decelerator 24, a rack gear 22' which engages with this pinion 21' being attached to a side surface 13a of the rotary gear 13. Although motion-communicating means using a pinion and a rack gear have been disclosed above, they may be replaced by a mechanism including a belt or a wire.

In summary, the present invention discloses improved apparatus for X-ray fluoroscopy and fluorography adapted to move a main body frame and a parallel-moving base vertically upward and downward along guide rails attached to a rotary gear and hence to be made compact and shorter in the front-to-back dimension.

What is claimed is:

1. An apparatus for X-ray fluoroscopy and fluorography comprising:

a supporting column for supporting means for radiating and detecting X-rays opposite each other;

a top board supporting means for supporting a top board above said means for detecting X-rays;

a base for supporting said top board supporting means movably vertically and rotatably around a horizontal axis;

a rotary member which is disposed between said top board supporting means and said base and is rotatable around said horizontal axis;

means for rotationally driving said rotary member;

guide rails extending vertically and attached to a side surface of said rotary member facing away from said base;

a parallel-moving base attached to said top board supporting means and movable along said guide rails; and parallel-moving means for causing said parallel-moving base to move vertically.

2. The apparatus of claim 1 further comprising a hollow horizontal shaft which is supported by said base and is rotatable around said horizontal axis, said parallel-moving means including a central rotary shaft which is supported inside said hollow horizontal shaft and is rotatable around said horizontal axis independently of said hollow horizontal shaft.

3. The apparatus of claim 2 wherein said parallel-moving means further include a pinion which is attached to one end of said central rotary shaft so as to rotate therewith, and a rack gear which engages with said pinion and is attached to said top board supporting means.

* * * * *